(12) United States Patent
Gopinath

(10) Patent No.: US 10,593,037 B2
(45) Date of Patent: Mar. 17, 2020

(54) METHOD, APPARATUS, AND SYSTEM TO IDENTIFY BRANCHES OF A BLOOD VESSEL

(71) Applicant: LightLab Imaging, Inc., Westford, MA (US)

(72) Inventor: Ajay Gopinath, Bedford, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 0 days.

(21) Appl. No.: 15/488,005

(22) Filed: Apr. 14, 2017

(65) Prior Publication Data

US 2017/0301084 A1 Oct. 19, 2017

Related U.S. Application Data

(60) Provisional application No. 62/322,771, filed on Apr. 14, 2016.

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/0066* (2013.01); *A61B 5/02007* (2013.01); *A61B 5/742* (2013.01); *G06T 5/002* (2013.01); *G06T 7/11* (2017.01); *G06T 7/13* (2017.01); *G06T 2200/24* (2013.01); *G06T 2207/10101* (2013.01); *G06T 2207/10132* (2013.01); *G06T 2207/20032* (2013.01); *G06T 2207/30021* (2013.01); *G06T 2207/30101* (2013.01)

(58) Field of Classification Search
None
See application file for complete search history.

(56) References Cited

U.S. PATENT DOCUMENTS

| | | |
|---|---|---|
| 4,548,473 A | 10/1985 | Lo et al. |
| 5,054,492 A | 10/1991 | Scribner et al. |

(Continued)

FOREIGN PATENT DOCUMENTS

| | | |
|---|---|---|
| EP | 2062526 | 5/2009 |
| JP | 63-127201 | 5/1988 |

(Continued)

OTHER PUBLICATIONS 3D assessment of stent cell size and side branch access inintravascular optical coherence tomographic pullback runs. Wang et al. 2012.*

(Continued)

*Primary Examiner* — Delomia L Gilliard
(74) *Attorney, Agent, or Firm* — K&L Gates LLP

(57) ABSTRACT

In part, the disclosure relates to an automated method of branch detection with regard to a blood vessel imaged using an intravascular modality such as OCT, IVUS, or other imaging modalities. In one embodiment, a representation of A-lines and frames generated using an intravascular imaging system is used to identify candidate branches of a blood vessel. One or more operators such as filters can be applied to remove false positives associated with other detections.

20 Claims, 9 Drawing Sheets
(8 of 9 Drawing Sheet(s) Filed in Color)

(51) Int. Cl.
  *G06T 7/13* (2017.01)
  *A61B 5/00* (2006.01)
  *A61B 5/02* (2006.01)
  *G06T 5/00* (2006.01)

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Corl et al. |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,822,391 A | 10/1998 | Whitting |
| 5,908,415 A | 6/1999 | Sinofsky |
| 5,947,959 A | 9/1999 | Sinofsky |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |
| 8,582,109 B1 | 11/2013 | Schmitt |
| 8,582,619 B2 | 11/2013 | Adler |

(56) References Cited

U.S. PATENT DOCUMENTS

| | | |
|---|---|---|
| 8,582,934 B2 | 11/2013 | Adler et al. |
| 8,670,603 B2 | 3/2014 | Tolkowsky et al. |
| 8,687,201 B2 | 4/2014 | Adler |
| 8,693,756 B2 | 4/2014 | Tolkowsky et al. |
| 8,700,130 B2 | 4/2014 | Iddan et al. |
| 8,781,193 B2 | 7/2014 | Steinberg et al. |
| 8,786,336 B1 | 7/2014 | Schmitt |
| 8,831,321 B1 * | 9/2014 | Elbasiony ............ A61B 5/0066 382/131 |
| 8,855,744 B2 | 10/2014 | Tolkowsky et al. |
| 8,909,323 B2 | 12/2014 | Baumgart |
| 8,913,084 B2 | 12/2014 | Chen et al. |
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony |
| 9,308,052 B2 | 4/2016 | Tolkowsky et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,488,464 B1 | 11/2016 | Schmitt |
| 9,629,571 B2 | 4/2017 | Tolkowsky et al. |
| 2002/0115931 A1 | 8/2002 | Strauss et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0201662 A1 | 9/2005 | Petersen et al. |
| 2005/0238067 A1 | 10/2005 | Choi |
| 2005/0249391 A1 | 11/2005 | Kimmel et al. |
| 2006/0095065 A1 | 5/2006 | Tanimura et al. |
| 2006/0135870 A1 | 6/2006 | Webler |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0024617 A1 | 2/2007 | Poole |
| 2007/0060822 A1 | 3/2007 | Alpert et al. |
| 2007/0066890 A1 | 3/2007 | Maschke |
| 2007/0115481 A1 | 5/2007 | Toth et al. |
| 2007/0123771 A1 | 5/2007 | Redel et al. |
| 2007/0135803 A1 | 6/2007 | Belson |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2007/0260198 A1 | 11/2007 | Atlas |
| 2007/0293932 A1 | 12/2007 | Zilla et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0228086 A1 | 9/2008 | Ilegbusi et al. |
| 2008/0281205 A1 | 11/2008 | Naghavi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank et al. |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1 | 9/2011 | Eichler |
| 2011/0257545 A1 | 10/2011 | Suri |
| 2011/0319752 A1 | 12/2011 | Steinberg et al. |
| 2012/0004529 A1 | 1/2012 | Tolkowsky et al. |
| 2012/0029339 A1 | 2/2012 | Cohen et al. |
| 2012/0057157 A1 | 3/2012 | Petersen et al. |
| 2012/0075638 A1 | 3/2012 | Rollins et al. |
| 2012/0162660 A1 | 6/2012 | Kemp |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2012/0310081 A1 | 12/2012 | Adler et al. |
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1 | 3/2016 | Svanerudh |
| 2016/0070066 A1 | 3/2016 | Schmitt et al. |
| 2016/0073885 A1 | 3/2016 | Adler |
| 2016/0174925 A1 | 6/2016 | Dascal et al. |
| 2016/0313507 A1 | 10/2016 | Adler et al. |
| 2016/0335763 A1 | 11/2016 | Ambwani et al. |
| 2016/0335766 A1 | 11/2016 | Ambwani et al. |
| 2017/0024910 A1 * | 1/2017 | Griffin .................. G06T 11/003 |
| 2017/0140243 A1 * | 5/2017 | Ambwani ............. G06T 7/0014 |

FOREIGN PATENT DOCUMENTS

| | | |
|---|---|---|
| WO | 2006076409 | 7/2006 |
| WO | 2007002685 | 1/2007 |
| WO | 2011038044 | 3/2011 |

(56) References Cited

FOREIGN PATENT DOCUMENTS

| WO | 2012176191 | 12/2012 |
|---|---|---|
| WO | 2013175472 | 11/2013 |
| WO | 2014002095 | 3/2014 |

OTHER PUBLICATIONS

Shape-Driven Segmentation of the Arterial Wall in Intravascular Ultrasound Images. Unal et al. 2008.*
Wang et al., "3D assessment of stent cell size and side branch access in intravascular optical coherence tomographic pullback runs", Computerized Medical Imaging and Graphics (38) 2014, pp. 113-122.
Unal et al., "Shape-Driven Segmentation of the Arterial Wall in Intravascular Ultrasound Images", IEEE Transactions on Information Technology in Biomedicine, vol. 12, No. 3, May 2008 pp. 335-347.
International Search Report and Written Opinion of the International Searching Authority for International application No. PCT/US2017/027680 mailed from the ISA dated Aug. 22, 2017 (20 pages).
Briguori et al., "Intravascular ultrasound criteria for the assessment of the functional significance of intermediate coronary artery stenoses and comparison with fractional flow reserve," Am J. Cardiol 87:136-141, 2001.
Kassab et al., "The pattern of coronary arteriolar bifurcations and the uniform shear hypothesis," Annals of Biomedical Engineering 23 (1): 13-20, 1995.
Hariri et al., "An automatic image processing algorithm for initiating and terminating intracoronary OFDI pullback" Biomedical Optics Express 1:2 566-573 (Sep. 1, 2010).
Harrison et al., "The value of lesion cross-sectional area determined by quantitative coronary angiography in assessing the physiologic significance of proximal left anterior descending coronary arterial stenoses," Circulation 69:6 1111-1119, 1984.
Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.
Kolyva et al., "Increased diastolic time fraction as beneficial adjunct of $\alpha 1$-adrenergic receptor blockade after percutaneous coronary intervention," Am J Physiol Heart Circ Physiol 295: H2054-H2060, 2008.
Kolyva et al., "'Windkesselness' of coronary arteries hampers assessment of human coronary wave speed by single-point technique," Am J Physiol Heart Circ Physiol, 295: H482-H490, 2008.
Laslett, "Normal left main coronary artery diameter can be predicted from diameters of its branch vessels," Clinical Cardiology 18 (10): 580-582, 1995.
Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.
Ohta et al., "Rheological Changes After Stenting of a Cerebral Aneurysm: A Finite Element Modeling Approach," Cardiovascular and Interventional Radiology (2005) 28:768-772.
Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.
Seiler et al., "Basic structure-function relations of the epicardial coronary vascular tree, Basis of quantitative coronary arteriography for diffuse coronary artery disease," Circulation 85 (6): 1987-2003, 1992.
Siebes et al., "Single-wire pressure and flow velocity measurement to quantify coronary stenosis hemodynamics and effects of percutaneous interventions," Circulation 109:756-762, 2004.
Sihan et al., "A Novel Approach to Quantitative Analysis of Intravascular Optical Coherence Tomography Imaging," Computers in Cardiology 2008; 35:1089-1092.
Sihan et al., "Fully Automatic Three-Dimensional Quantitative Analysis of Intracoronary Optical Coherence Tomography: Method and Validation," Catheterization and Cardiovascular Interventions 74:1058-1065 (2009).
Spaan, "Coronary Blood Flow," Ch 12. Dordrecht, The Netherlands: Kluwer Acedemic Publishers, Boston; 1991: pp. 333-361.
Takagi et al., "Clinical potential of intravascular ultrasound for physiological assessment of coronary stenosis," Circulation 100: 250-255, 1999.
Verhoeff et al., "Influence of percutaneous coronary intervention on coronary microvascular resistance index," Circulation 111:76-82, 2005.
White et al., "Does visual interpretation of the coronary angiogram predict the physiologic importance of coronary stenoses?," N. Engl J Med 310:13 819-824, 1984.
Wilson et al., "Prediction of the physiologic significance of coronary arterial lesions by quantitative lesion geometry in patients with limited coronary artery disease," Circulation 75: 723-732, 1987.
Perez-Rovira et al., "Deformable Registration of Retinal Fluorescein Angiogram Sequences Using Vasculature Structures", 32nd Annual Conf. of IEEE EMBS, 2010, pp. 4383-4386.
Herrington et al., "Semi-automated boundary detection for intravascular ultrasound," Computers in Cardiology 1992 Proceedings., pp. 103-106, Oct. 1992.
Sonka et al., "Segmentation of intravascular ultrasound images: a knowledge-based approach," IEEE Transactions on Medical Imaging, 14(4):719-732, Dec. 1995.
Mojsilovic et al., "Automatic segmentation of intravascular ultrasound images: A texture-based approach," Annals of Biomedical Engineering, 25:1059-1071, Nov. 1997.
Gil et al., "Automatic segmentation of artery wall in coronary IVUS images: a probabilistic approach," Computers in Cardiology 2000; 27:687-690.
Haas et al., "Segmentation of 3D intravascular ultrasonic images based on a random field model," Ultrasound in Medicine & Biology, 26:2, 297-306, 2000.
Kovalski et al., "Three-dimensional automatic quantitative analysis of intravascular ultrasound images," Ultrasound in Medicine & Biology, 26(4):527-537, 2000.
Pujol et al., "Intravascular Ultrasound Images Vessel Characterization using AdaBoost," Functional Imaging and Modeling of the Heart: Lecture Notes in Computer Science, pp. 242-251, 2003.
Taki et al., "Automatic segmentation of calcified plaques and vessel borders in IVUS images," International Journal of Computer Assisted Radiology and Surgery, 3(3-4):347-354, Sep. 2008.
Van den Berg et al., "Using three-dimensional rotational angiography for sizing of covered stents," Am. J. Roentgenology, 178:149-152 (2002).
Wong et al., "A novel method of coronary stent sizing using intravascular ultrasound: safety and clinical outcomes," Int. J. Angiol. , 18(1): 22-24 2009.
Bonnema et al., "An automatic algorithm for detecting stent endothelialization from volumetric optical coherence tomography datasets", Physics in Medicine and Biology, 53 :12, Jun. 21, 2008, pp. 3083-3098.
Unal et al., "Stent implant follow-up in intravascular optical coherence tomography images," Int J Cardiovasc Imaging, DOI 10.1007/s10554-009-9508-4, published online Sep. 24, 2009, 8 pgs.
Xu et al., "Characterization of atherosclerosis plaques by measuring both backscattering and attenuation coefficients in optical coherence tomography," Journal of Biomedical Optics, 13:3, May/Jun. 2008, 8 pgs.
Takano et al.. "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.
Tung et al., "Automatic Detection of Coronary Stent Struts in Intravascular OCT Imaging," Proceedings of SPIE, vol. 8315, Feb. 22, 2012 (8 pgs.).

(56) References Cited

OTHER PUBLICATIONS

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Dave Fornell, "The Advantages and Disadvantages of OCT vs. IVUS", Diagnostic and Interventional Cardiology, May 18, 2011, pp. 1-4.

* cited by examiner

METHOD, APPARATUS, AND SYSTEM TO IDENTIFY BRANCHES OF A BLOOD VESSEL

CROSS REFERENCE TO RELATED APPLICATIONS

This application claims priority to and the benefit of U.S. Provisional Patent Application No. 62/322,771 filed on Apr. 14, 2016, the disclosure of which is herein incorporated by reference in its entirety.

FIELD

The disclosure relates generally to systems and methods suitable for use in the field of intravascular diagnostics and imaging, more specifically to systems and methods that support identifying side branches, junctions or other sections or features of a blood vessel.

BACKGROUND

Coronary artery disease is one of the leading causes of death worldwide. The ability to better diagnose, monitor, and treat coronary artery disease can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution.

Viewing subsurface structures with high resolution using fiber-optic probes makes OCT especially useful for minimally invasive imaging of internal tissues and organs. This level of detail made possible with OCT allows a clinician to diagnose, as well as monitor, the progression of coronary artery disease. OCT images provide high-resolution visualization of coronary artery morphology and can be used alone or in combination with other information such as angiography data and other sources of subject data to aid in diagnosis and treatment planning.

OCT imaging of portions of a patient's body provides a useful diagnostic tool for doctors and others. For example, imaging of coronary arteries by intravascular OCT may reveal the location of a narrowing or stenosis, which reduce blood flow and increase the risk of ischemia. This information helps cardiologists to choose between an invasive coronary bypass surgery and a less invasive catheter-based procedure such as angioplasty or stent delivery to mitigate the stenosis and restore blood flow. The presence of arterial side branches in the stenosis region also affects blood flow through the artery, and therefore is an important factor when designing a treatment plan for the patient.

The quantitative assessment of vascular pathology and its progression involves the calculation of different quantitative measures such as pressure drops which can rely on the accurate identification of fluid flow and geometry of the lumen, including side branch geometry. Side branches extending from a lumen in OCT images are often not easily identified. In part, this results because side branches can be obscured by the guidewire used in various OCT probes or otherwise obscured by stent struts, blood, and shadows.

Further, shadows and other imaging data artifacts can be challenging to resolve and eliminate. As a result, important landmarks along the length of an artery such as side branches can be mistaken for tissue or simply not identified. Given that placing a stent over a side branch can be damaging or when performed, it should be done knowingly, there is a need for a reliable technique that can identify side branches.

The present disclosure addresses these challenges and others.

SUMMARY

In part, the disclosure relates to a method of detecting one or more branches of a blood vessel. The method includes storing one or more intravascular image datasets of the blood vessel, each intravascular dataset comprising a plurality of A-lines; detecting a lumen boundary in a first A-line image generated from a set of A-lines from the plurality of A-lines, wherein the first A-line image has an r dimension and an A-line dimension; specifying a search distance T; defining a search region, the search region bounded by the detected lumen boundary and a boundary offset therefrom by distance T; detecting edges in the search region; and identifying candidate branching region in response to the detected edges.

In one embodiment, the method includes flattening the A-line image using a first image processing operator; applying median smoothing to A-line image using a second image processing operator; and applying smoothing to A-line image using a third image processing operator to generate a filtered image. In one embodiment, the method includes identifying a first minimum-maximum pair in the filtered image, wherein one or more distances between the first minimum-maximum pair defines a first search window. In one embodiment, the method includes identifying a second minimum-maximum pair in the filtered image, wherein one or more distances between the second minimum-maximum pair defines a second search window.

In one embodiment, the method includes searching along r dimension in corresponding pre-processed input image within first search window. In one embodiment, the method includes designating pixels below noise floor threshold located in the first search window as corresponding to the candidate branching region. In one embodiment, noise floor threshold is less than about 2 mm. In one embodiment, the method includes splitting the candidate branch region into three bands, wherein sum of widths of three bands is equal to T. In one embodiment, the method includes for each band, accumulating pixels along each A-line that correspond to the candidate branching region.

In one embodiment, the method includes wherein if a particular A-line has more than between about 10% and about 30% pixels marked as a candidate branch, mark that A-line in that band as corresponding to a branch. In one embodiment, the method includes outputting set of A-lines for each band that correspond to a candidate branch.

In one embodiment, the method includes generating a branching matrix using frames of a pullback, the frames comprising A-lines and angular data. In one embodiment, the method includes isolating pixels corresponding to a grouping of all three bands and a grouping of first two bands to select pixels corresponding to a side branch. In one embodiment, the method includes removing a guidewire region from the branching matrix. In one embodiment, the method includes eliminating branches that appear only in one frame. In one embodiment, the method includes replicating branching matrix to account for overlap across zero.

In one embodiment, the first band ranges from 0 to T/3, and wherein second band ranges from T/3 to ⅔T, and wherein third band ranges from ⅔T to T. In one embodiment, the first band ranges from 0 to T/3, and wherein second band ranges from T/3 to ⅔T, and wherein third band ranges from ⅔T to T. In one embodiment, the method includes displaying one or more detected side branches in a user interface. In one embodiment, the method includes validating one or more candidate side branches using a branching matrix, the branch matrix generated using pixel selected from two or more bands, wherein the sum of the bands is T.

Other features and advantages of the disclosed embodiments will be apparent from the following description and accompanying drawings.

BRIEF DESCRIPTION OF DRAWINGS

The patent or application file contains at least one drawing executed in color. Copies of this patent or patent application publication with color drawing(s) will be provided by the Office upon request and payment of the necessary fee.

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Figure 1:
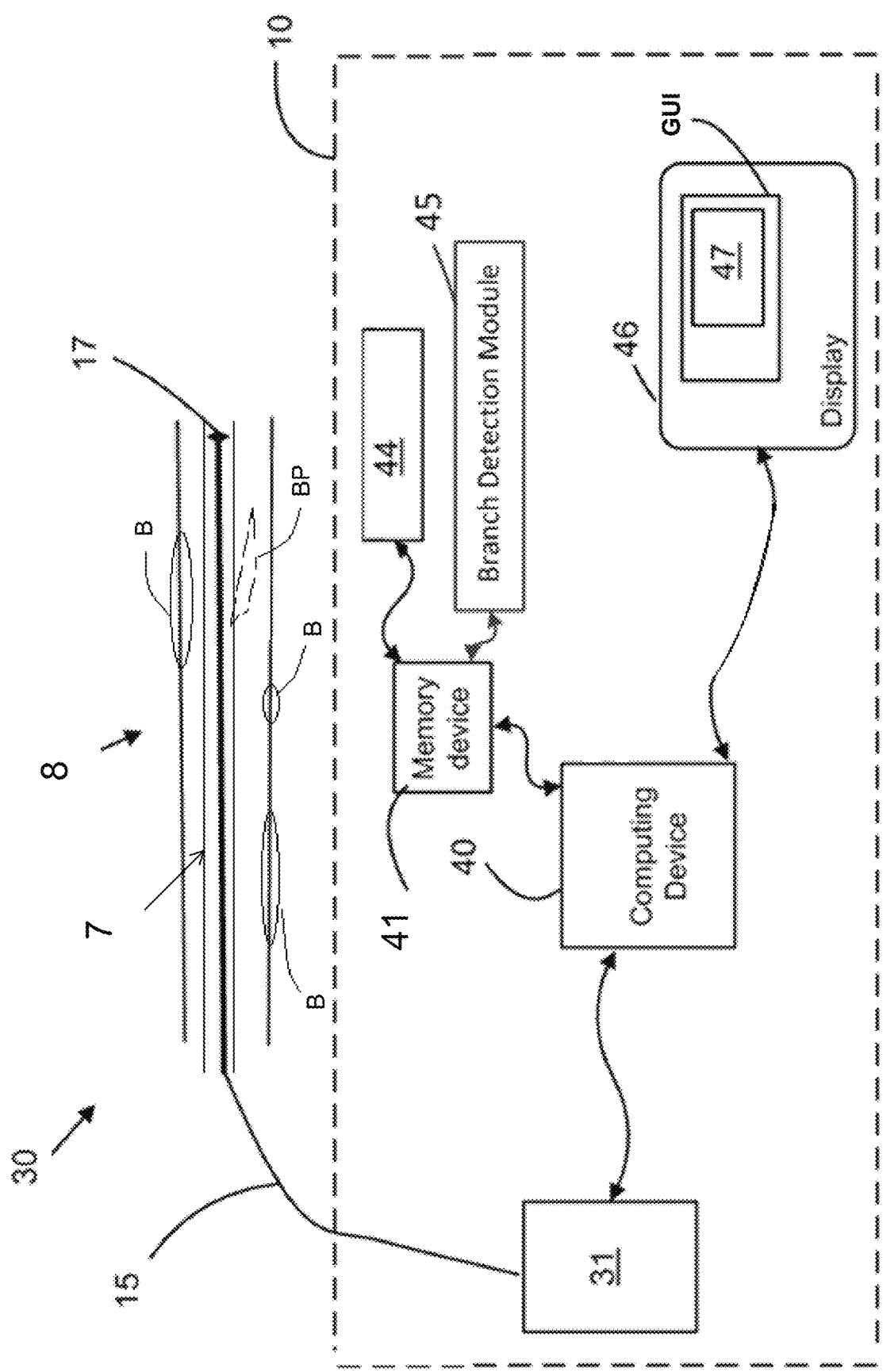
FIG. 1 is a diagram of an intravascular imaging system, including automated side branch detection module according to an illustrative embodiment of the disclosure.

In part, the disclosure relates to an automated method of branch detection with regard to a blood vessel imaged using an intravascular modality such as OCT, IVUS, or other imaging modalities. The term branch refers to one or more branches of a blood vessel such as a side branch. In one embodiment, the disclosure relates to performing branch detection as an intermediate step in a pipeline of software modules, operators, and stages. The various stages transform intravascular data and perform feature detection such as shadow and lumen detection thereon. Branch detection can be performed after an OCT or IVUS pullback and the resulting intravascular data can be processed using a lumen detection software module to extract lumen data such as information relating to a lumen boundary.

In part, the invention relates to various methods of collecting and processing data such as frames of intravascular data. In one embodiment, a frame of intravascular data or image data includes a cross-sectional image generated from a plurality of A-lines (scan lines) obtained using a rotatable intravascular probe. A cross-sectional image of blood vessel is formed by a collection of scan lines as the probe rotates.

In one embodiment, prior to branch detection, shadow detection is performed to identify regions of interest from the underlying intravascular data. Shadows are of interest because they can correspond to different features such as blood pools, branches such as side branches, and guidewire segments. Guidewire segments arise from the guidewire used to position the intravascular imaging probe in the artery. In one embodiment, once a guidewire (or guidewires) have been identified and validated, guidewire generated positional or pixel markings on a given frame or scan line can be provided to other intravascular data processing modules. As an example, validated guidewire detections can be an input to a side branch detection module. The process of detecting side branches can also be input into other processing stages to generate information of interest with regard to the intravascular pullback data.

In part, the disclosure describes various methods and sub-methods relating to branch detection and the evaluation of parameters relating thereto. In one embodiment, the method is an automated method that operates upon intravascular data based on a user interface input to detect side branches or as part of other image processing that uses side branch detections as inputs.

Side branches in coronary arteries can be used to model the normal diameter of the artery at each segment as the artery tapers. The location and diameter of the side branch is an important input to calculate and predict flow along the artery.

A new software algorithm has been developed that will automatically detect the location of side branches in OCT images and provide an estimate of its diameter. The algorithm will identify the frames and the scan lines of OCT frames that are part of the branching region.

In one embodiment, the software-based methods work on scan lines in polar coordinate space and use a combination of image processing filters and algorithms to detect the rising and falling intensity gradients of the side branch wall. In one embodiment, the software generates a matrix from scan line data that is organized based on frames along the pullback. The matrix includes data from the pull-back that collects information beyond the lumen by an offset amount or other distance extending into the tissue or side branches. This matrix (Branching Matrix) is parsed to get information about possible branch locations and is used to measure the branch diameters.

As shown in FIG. 1, a data collection system 30 for use in collecting intravascular data includes a data collection probe 7 that can be used to image a blood vessel. The system can be an OCT, IVUS, or other intravascular imaging modality-based system. A guidewire can be used to introduce the data collection probe 7 into the blood vessel. The data collection probe 7 can be introduced and pulled back along the blood vessel while collecting data. As the imaging probe is retracted (pulled-back) along the length of the vessel, a plurality of scans or intravascular data sets (OCT, IVUS, or other data) are collected as the probe or a portion thereof rotates. This is referred to as a pullback in one embodiment.

In one embodiment, these data sets, or collections of frames of image data, can be used to identify regions of interest such as a stenosis or a deployed stent. In one embodiment, the data collection probe 7 is an OCT probe. The probe 7 can include a probe tip 17. When an OCT probe is used for probe 7, it is configured for use with a version of system 10 that includes an interferometer and a data processing system. The distance measurements collected using the data collection probe 7 can be processed to generate frames of image data such as cross-sectional views or longitudinal views (L-mode views) of the blood vessel. For clarity, a cross-sectional view can include without limitation a longitudinal view. These images can be processed using one or more image data processing modules or stages.

The data collection probe 7 is shown prior to or after insertion in a blood vessel. The data collection probe 7 is in optical communication with an OCT system 10. The OCT system 10 that connects to data collection probe 7 via an optical fiber 15 can include a light source such as a laser, an interferometer having a sample arm and a reference arm, various optical paths, a clock generator, photodiodes, and other OCT system components. The probe 7 is disposed in an artery 8 having branches B and blood pools BP.

In one embodiment, an optical receiver 31, such as a balanced photodiode based system, can receive light exiting the data collection probe 7. A computing device 40 such as a computer, processor, ASIC, or other device can be part of the OCT system 10 or can be included as a separate subsystem in electrical or optical communication with the OCT system 10. The computing device 40 can include memory device(s) 41, storage, buses and other components suitable for processing data and software components 44 such as image data processing stages configured for stent visualization, stent malapposition detection, lumen detection, offset generation, search region 151 definition, side branch detection 45, guidewire detection, branching matrix generation, pullback data collection and others. Although the branch detection module 45 is shown as a separate software module it can also be one of the software components 44. The branching matrix generation software can be part of the branch detection module 45 or be a separate software module.

In various embodiments, the computing device 40 includes or accesses software modules or programs 44, such as a side branch detection module, a guidewire detection module, a lumen detection module, a stent detection module, a median mask clearing module, an intensity averaging module, a stent malapposition detection module, a carina detection module, and other software modules. For example, the computing device 40 can access a side branch detection module 45 for detecting side branches. In particular, the module is calibrated to use certain branching characteristics as signatures to improve branching accuracy.

In one embodiment, the side branch detection module 45 generates or operates upon a two dimensional branching matrix and isolates candidate side branches using the matrix or as otherwise described herein. In one embodiment, the branching characteristics can include an arrangement of intravascularly detected features such as a noise floor and rising or falling gradients. The software modules or programs 44 can include an image data processing pipeline or component modules thereof and one or more graphical user interfaces (GUI).

An exemplary image processing pipeline is used for transforming collected intravascular data into two dimensional and three dimensional views of blood vessels and stents. The image data processing pipeline or any of the methods described herein are stored in memory and executed using one or more computing devices such as a processor, device, or other integrated circuit.

In one embodiment, the software modules 44 also includes additional features relating to blood flow detection or includes such features in lieu of side branch detection. In one embodiment, the diameter of one or more side branches and predicting blood flow across these side branches. The software modules 44 can also include or be in communication with user interface software components to toggle side branch blood flow views on and off and to display and toggle the various user interface display modes such as stent planning, fly through and other viewing modes described herein.

As shown in FIG. 1, a display 46 can also be part of an intravascular data collection and processing system 10 for showing information 47 such as cross-sectional and longitudinal views of a blood vessel generated using collected image data.

Data collection system 10 can be used to display image data relating to blood flow associated with detected side branches for the vessel. In one embodiment, one or more steps can be performed automatically or without user input other than initial user input to navigate relative to one or more images, enter information, select or interact with an input such as a controller or user interface component, or otherwise indicate one or more system outputs. In one embodiment, a blood flow view is presented as an option to select to facilitate review of a two or three-dimensional view of a representation of the vessel and one or more side branches. Toggling between one or more viewing modes in response to user inputs can be performed relative to various steps described herein.

Representations of a stent and a lumen boundary such as OCT or IVUS images thereof can be shown to a user via display 46. Side branch detection, shadow detection and stent detection are performed prior to the display of these features and any coding or tagging with identifying indicia that may be included in the displayed image. This OCT-based information 47 can be displayed using one or more graphic user interface(s) (GUI). The images of FIGS. 14A, 14B, and 22-26 are examples of information 47 that can be displayed and interacted with using a GUI and various input devices.

In addition, this information 47 can include, without limitation, cross-sectional scan data, longitudinal scans, diameter graphs, image masks, shadow regions, stents, areas of malapposition, lumen border, perpendicular distances measured relative to a automatically detected lumen border and a perpendicular distance extending from the lumen border having a distance T, and other images or representations of a blood vessel or the underlying distance measurements obtained using an OCT system and data collection probe.

The computing device 40 can also include software or programs 44, which can be stored in one or more memory devices 41, configured to identify stent struts and malapposition levels (such as based on a threshold and measured distance comparison) and other blood vessel features such as with text, arrows, color coding, highlighting, contour lines, or other suitable human or machine readable indicia.

The display 46 depicts various views of the blood vessel, in accordance with an embodiment. The display can include a menu for showing or hiding various features, such as a menu for selecting blood vessel features to display, and a menu for selecting the virtual camera angle of the display. The user can toggle between multiple view angles on the user display. In addition, the user can toggle between different side branches on the user display, such as by selecting particular side branches and/or by selecting a view associated with a particular side branch.

For example, the user can select an ostium view, which can be the default view in one embodiment or a carinal/carina view to allow them to view a carina for one or more side branches. In one embodiment, the image processing pipeline and associated software modules detect the lumen boundary, guidewires, other shadows, stents, and the side branches in the artery imaged using the data collected during a pullback.

For example, the lumen boundary can be detected using the distance measurements obtained from the optical signals collected at the probe tip 17 using a lumen detection software component or module. In lieu of a fiber, an ultrasound transducer can be used suitable for collecting IVUS signals with regard to the vessel wall and one or more stents.

The lumen detection software can include one or more steps. For example, to perform lumen detection in one embodiment a filter or other image processing device can be applied to a two dimensional image to detect edges in the images, the edges indicative a lumen boundary. In another embodiment, a scan line based approach is used. During one or more pullbacks, optical or ultrasound signals are collected as scan lines with respect to a blood vessel and one or more stents disposed in the lumen of the vessel. In one embodiment, the lumen detection software executing a computing device generates one or more images from the set of scan lines using a computing device.

Further, lumen detection can include generating a binary mask of the vascular image using the computing device, wherein the binary mask is generated using an intensity threshold. As another step, a plurality of scan lines is defined in the binary mask. With regard to each scan line of the plurality of scan lines, in one embodiment, a region is identified as lumen boundary tissue thereon. Contour segments of the boundary are identified based on the presence of a region of lumen boundary tissue. In one embodiment, the method identifies neighboring contour segments. The lumen boundary detection method can also include interpolating missing contour data between neighboring contour segments. As a result, in one embodiment, the neighboring contour segments and the interpolated missing contour data define the lumen boundary.

Once the intravascular data, such as frames and scan lines from the pullback, is obtained with a probe and stored in memory 41, it can be processed to generate information 47 such as a cross-sectional, a longitudinal, and/or a three-dimensional view of the blood vessel along the length of the pullback region or a subset thereof. These views can be depicted as part of a user interface as shown in the figures. The images of the blood vessel generated using the distance measurements obtained from the intravascular data collection system provide information about the blood vessel and objects disposed therein.

Accordingly, in part, the disclosure relates to software-based methods and related systems and devices suitable for evaluating and depicting information regarding a blood vessel, a stent or other vascular information of interest. The intravascular data can be used to generate 2-D views such as cross-sectional and longitudinal views of a blood vessel before or after an initial stent deployment or corrective stent related procedure. The intravascular data obtained using a data collection probe and various data processing software modules can be used to identify, characterize, and visualize a stent and/or one or more properties relating to the stent and/or the lumen in which it is disposed.

Stent position relative to the wall of the blood vessel and in relation to openings for side branches in the wall of the blood vessel can be visualized such that the side branch openings are not blocked by the stent. In one embodiment, side branches are identified and visualized to aide in treatment planning and stent placement.

Figure 2A:
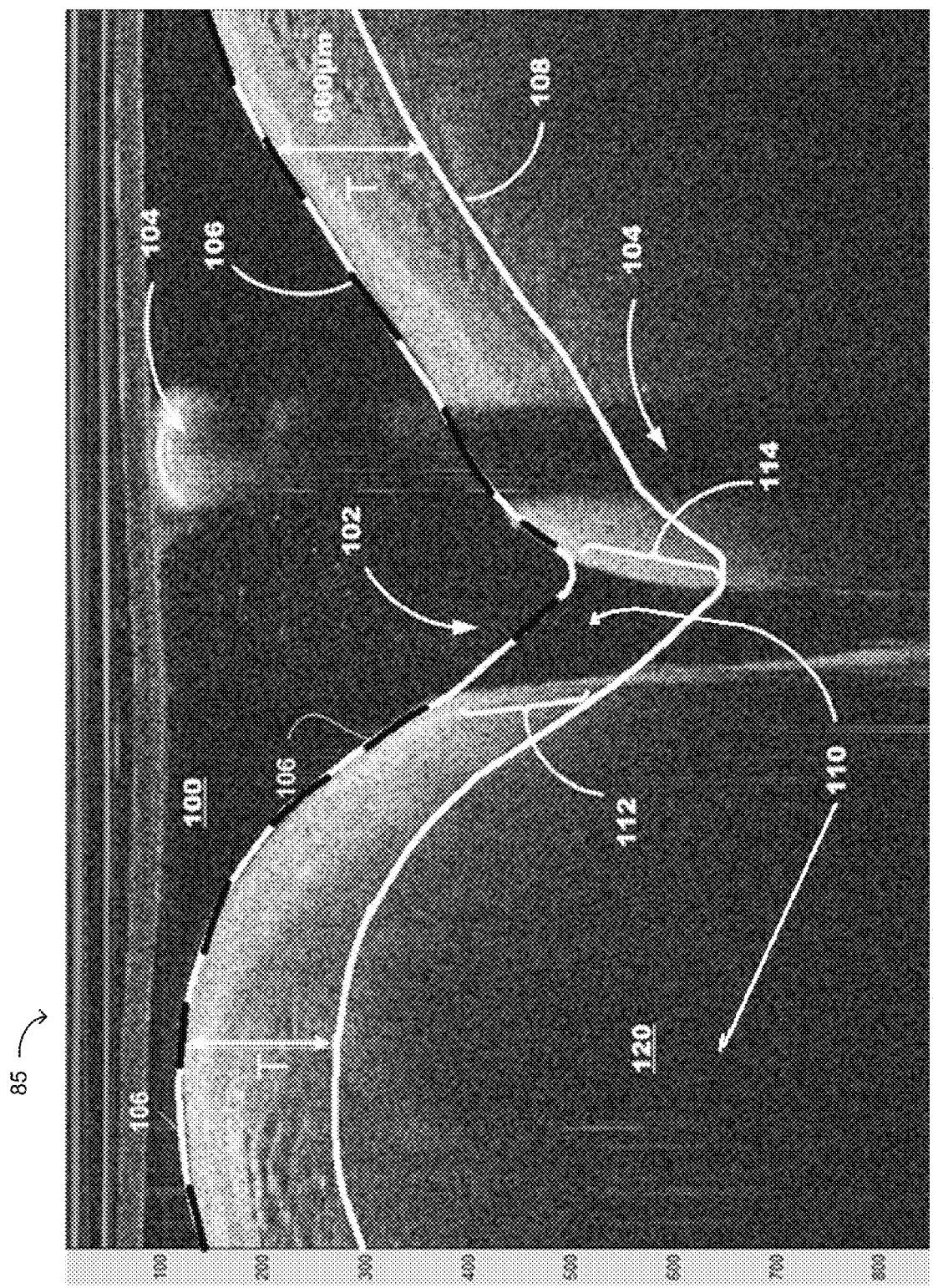
FIG. 2A is a polar, A-line image of a region of interest in a blood vessel having a side branch according to an illustrative embodiment of the disclosure.

FIG. 2A is a polar A-line OCT image of a region of interest in a blood vessel having a side branch 102. The blood vessel lumen 100 is at the top of the image. The lumen boundary 106 (i.e., the edge of the blood vessel wall) is demarcated by dotted line as shown, and blood vessel wall tissue 120 fills most of the image. The guidewire shadow 104 is the vertical feature on the right side of the image. In the image, lumen boundary 106 provides the brightest response, and the OCT signal attenuates to a tissue penetration depth. Side branches 102 appear as vertical shadows, or signalless regions, in the blood vessel wall. In part, the disclosure relates to detecting side branches such as branch 102.

In one embodiment, guidewire detection is performed initially such that shadows and guidewire segments can be excluded from side branch shadows to increase detection accuracy. In various embodiments, the intravascular data collection system and associated software modules detects branching characteristics in the OCT image data within a predetermined scan depth region T. The T value can be used to define a search region 151. The T value can be input via a graphic user interface.

Figure 2B:
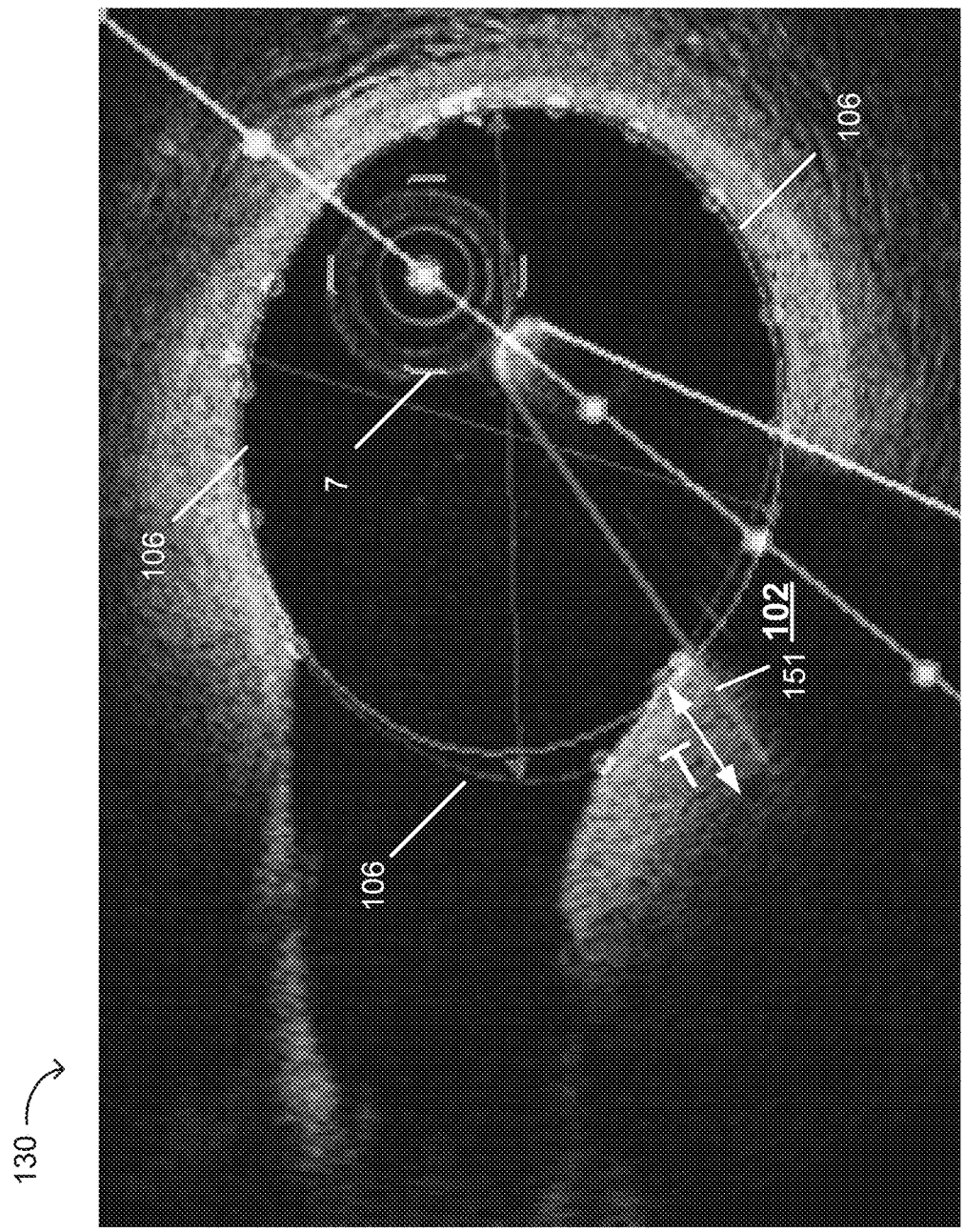
FIG. 2B is cross-sectional image of blood vessel corresponding to the A-line image of FIG. 2A according to an illustrative embodiment of the disclosure.

In one embodiment, T is specified as about 660 µm and is used as an offset from the lumen to define an offset lumen boundary demarcated by line 108. The region of interest/searching for branch detection is defined, in one embodiment, by the line 108, which is the lumen boundary 106 shifted by distance T and lumen boundary 106. The curved strip or ribbon 151 of width T bounded by dotted line (lumen boundary 106) and shifted lumen boundary 108 specifies a subset of intravascular image data to search for side branches. T can range from about 500 µm to about 800 µm. FIG. 2B is cross-sectional image 130 of blood vessel corresponding to the A-line image 85 of FIG. 2A. In FIG. 2B, the lumen boundary 106 is shown relating to probe 7 and side branch 102. A portion of the search region 151 adjacent side branch 102 is shown. Region 102 is an example of a branching region detectable using one or more methods and systems described herein.

Branch Detection Embodiment

The software-based branching method first scans for a branching signature or pattern defined by a noise floor 110 (also referred to as NF), or a signalless region, between a falling response gradient 112 and rising response gradient 114. In one embodiment, the noise floor is the zone or region in which the tissue intensity has dropped off to the same value as in the cleared lumen. The noise floor 110 can correspond to the transitional region in between rising and falling intensity gradients in a search zone or region. Next, any image frames that fit this signature or pattern are marked as candidate branching regions. Candidate branching regions are then combined across all frames. In turn, the branching regions are optionally parsed relative to a branching matrix and the diameter of each side branch is estimated. The software-based branching method is described in more detail herein.

Figure 3:
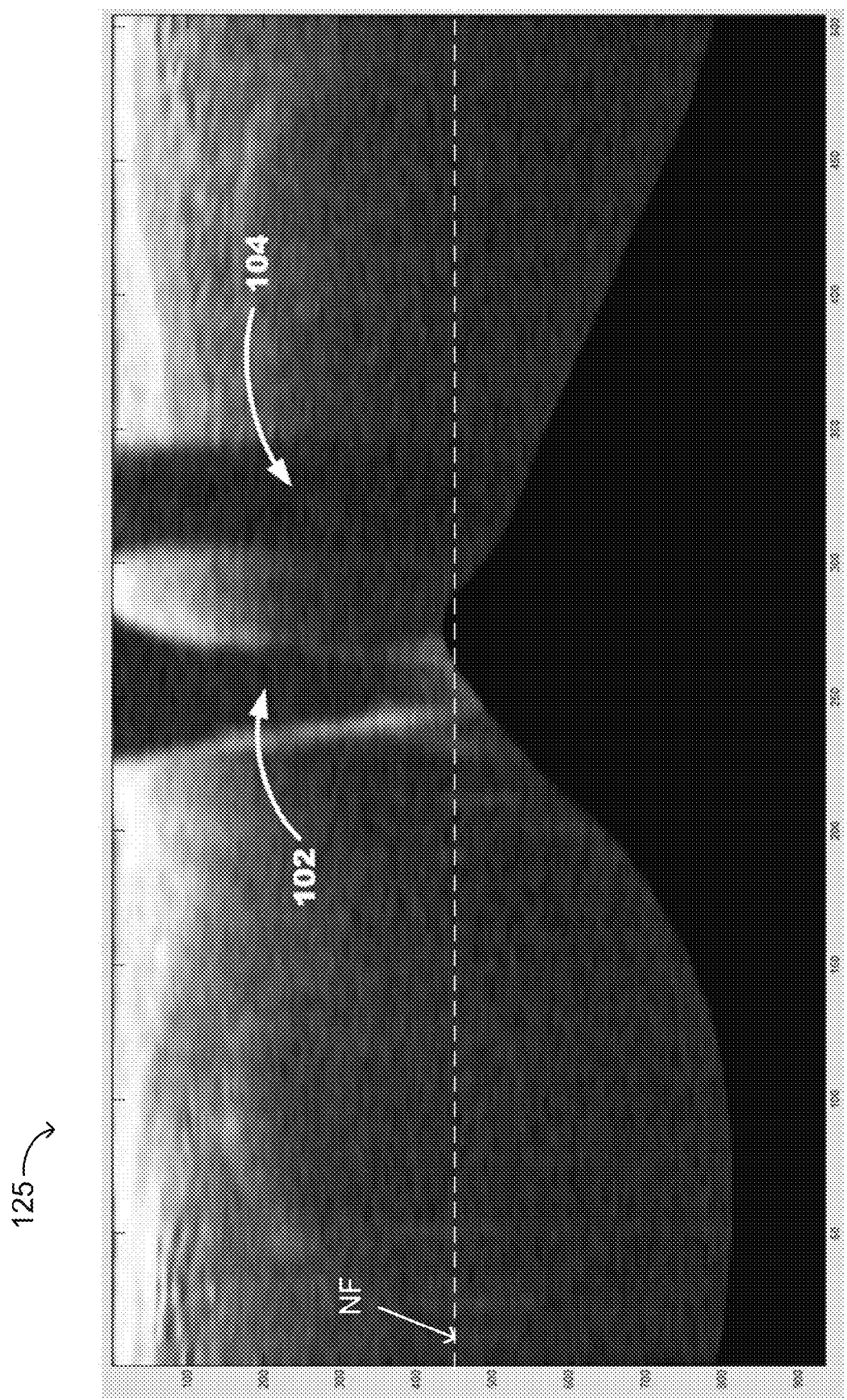
FIG. 3 is a flattened version of the image shown in FIG. 2A according to an illustrative embodiment of the disclosure.
Figure 4:
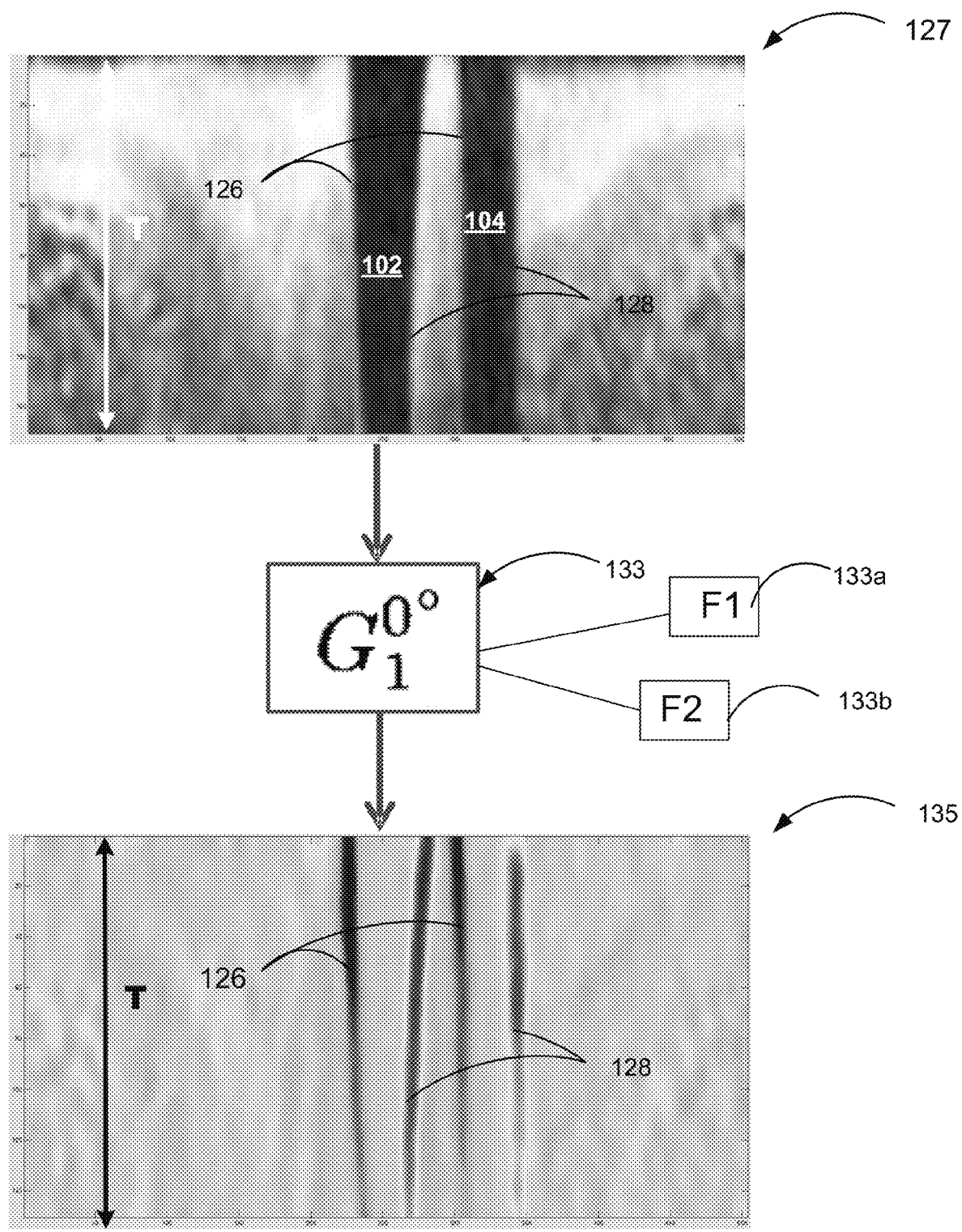
FIG. 4 is an image showing edge detection of a side branch according to an illustrative embodiment of the disclosure.

Initially, after a pullback, raw A-line images are pre-processed to flatten the images, making it easier to identify side branches. FIG. 3 is an intravascular image 125 that is a flattened version of the image shown in FIG. 2A. A-line images are flattened using the detected lumen boundary (106 in FIG. 2A) as the top edge of the flattened image. Image 127 also can be filtered using median and Gaussian image smoothing as shown in FIG. 4.

The pre-processed image 125 of FIG. 3 is analyzed to detect the noise floor NF. The noise floor NF can be used as a threshold to identify pixels below the noise floor as candidate branching regions. The noise floor threshold is computed based on an image histogram or known OCT noise levels from different samples. In one embodiment, the noise floor is determined to be from about 1.5 mm to about 2.5 mm from the lumen in the direction of the T offset. In one embodiment, the noise floor is about 2 mm.

In one embodiment, a portion of the flattened image 125 of FIG. 3 containing a candidate side branch is then processed using an edge detection filter 133 or filter F1 or F2. To reduce data processing and improve efficiency, filtering preferably is performed on data corresponding to the predetermined scan depth T. In the FIG. 4, the scan depth T is 660 μm from the lumen boundary, but any depth compatible with OCT can be used. Image 127 is filtered using filter 133 to generated filtered image 135. An edge detection filter can be applied to identify the left edges 126 and right edges 128 of the side branch and guidewire shadow. In one embodiment, the filter 133 is a Gaussian filter. In one embodiment, filter 133 is two filters such as filters 133a, 133b also referred as a first filter F1 and a second filter F2. In one embodiment, filters 133a, 133b are one or more separable edge finding filters. In one embodiment, the edge finding filters used herein are boxcar type filters.

Further, in one embodiment the filter is a smoothing filter. In one embodiment, the filter 133 is an edge finding filter. In one embodiment, the filter 133 is a combination smoothing and an edge finding filter which can be filters F1 and F2.

Figure 5A:
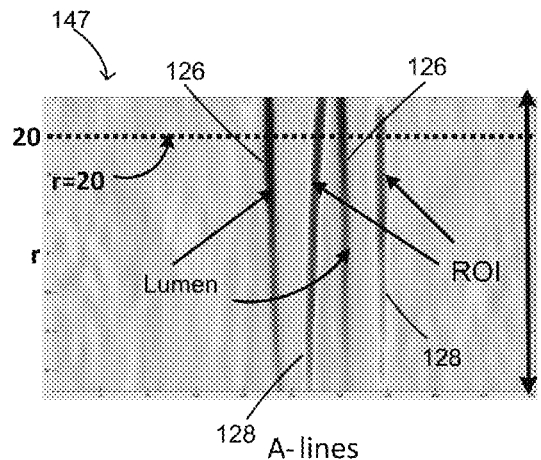
FIGS. 5A-5D are image processed A-line images after flattening in which a radial dimension r is perpendicular to an A-line dimension and various plots relative to a noise floor for different r values according to an illustrative embodiment of the disclosure.

As an additional step, an edge filtered image such as image 135 of FIG. 4 is analyzed along various r values as shown as image 147 as shown in FIG. 5A. In FIG. 5A, the images 147 is then analyzed for each r dimensional value for all or a subset of all A-lines to detect candidate branching regions. In turn, image 147 is filtered for each r value or a subset thereof by filtering it along the r=20 value. In this way, the filter plot 149 of FIG. 5B identifies local min-max peaks in filtered image 149 of FIG. 5B for r=20. This process is repeated for all or a subset of the r values in one embodiment to generate a set of local min-max peaks.

As shown in FIG. 5A, a region of interest (ROI) 128 is shown relative to lumen 126. The ROI corresponds to the detected lumen 126 portion that is shifted by T. The vertical axis of FIGS. 5A and 5C corresponds to an r dimension, with one dotted line at r=20 being illustrated that passes through the pair of lumen signals 126 and the pair of ROI signals 128. Between the min-max pair indices, which are shown by the circled max and min values in the filtered image plot of FIG. 5B and the pre-processed input image intensity plot of FIG. 5D.

Figure 5B:
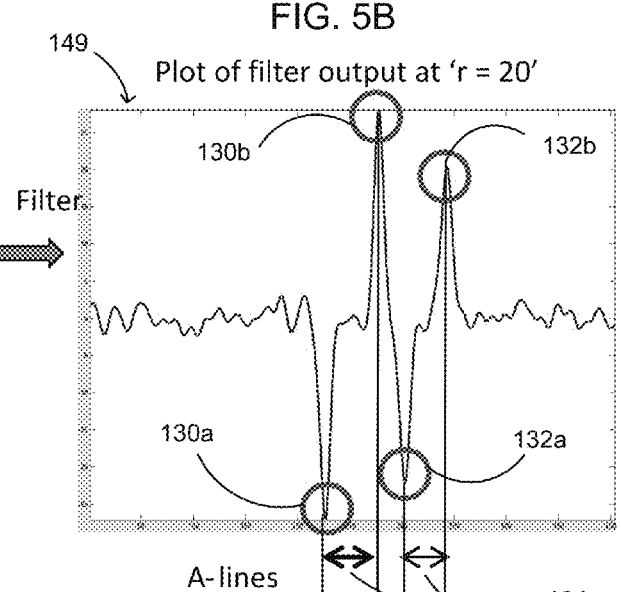
Figure 5C:
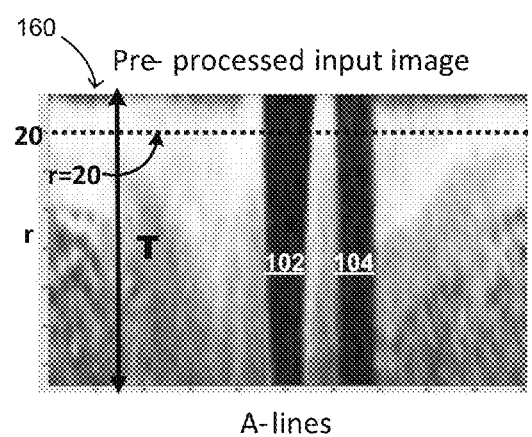
Figure 5D:
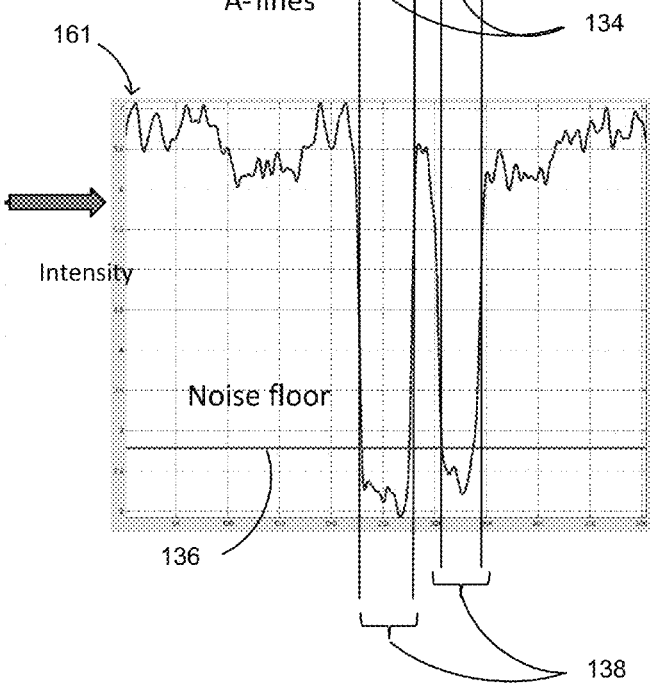

With regard to FIG. 5B, the vertical axis of the plot is the filter output resulting from filtering FIG. 5A and the horizontal axis A-lines. FIG. 5D is an intensity plot of the pre-processed image of FIG. 5C. In FIG. 5D, the vertical axis is the input image intensity. In one embodiment, the system searches along the 'r' dimension in the corresponding pre-processed input image for all or a subset of the r values which spans the A-lines of the image.

The noise floor of FIG. 3 is also shown in the intensity plot of FIG. 5D. The noise floor sets a threshold below which candidate side branches 138 are identified. In one embodiment, the noise floor threshold is based on the estimate of the noise floor and set such that samples near the noise floor are less than this threshold while tissue samples are guaranteed to be greater than it. The system uses one or more software components to look for pixels below the noise floor threshold which is specified in plot 161 of FIG. 5D in the corresponding regions of the flattened image (FIG. 5C). Referring to FIG. 5A, an edge filtered image 147 is filtered to identify local maxima and local minima at "r=20." In one embodiment, this filtering and plotting of the filtered result is performed for all or a subset of the r values. The r values are along vertical axes in FIGS. 5A and 5C. In FIG. 5B, the x axis corresponds to A-line number and the y axis corresponds to r. Referring to FIG. 5B, the min-max method identifies respective local min-max pairs 130a, 130b and 132a, 132b as shown.

Further, with regard to FIG. 5B, the method searches the plot 149 within value range 134 between each min-max pair for a noise floor in the corresponding flattened image 160 of FIG. 5C. Intravascular data from the flattened image are plotted as A-line (x axis) vs. intensity (y axis) to identify the scan lines containing the weakest OCT response. The regions of the flattened image falling below a predetermined threshold 136 are considered candidate branching regions 138. In one embodiment, the threshold 136 is the noise floor (NF). Thus, a local minimum 130a, 132a (lower set of circled values) typically will be found in a falling response gradient (112 in FIG. 2A) and a local maximum 130b, 132b (upper set of circled value) typically will be found in a rising response gradient (114 in FIG. 2A).

In one embodiment, the occurrence of a peak and a trough corresponds to a change in gradient intensity that defines a search space. If there is a signal below the noise floor in the search space then the corresponding pixels correspond to candidate branching regions. These candidate regions are subsequently analyzed to determine if they are valid side branches.

Figure 6:
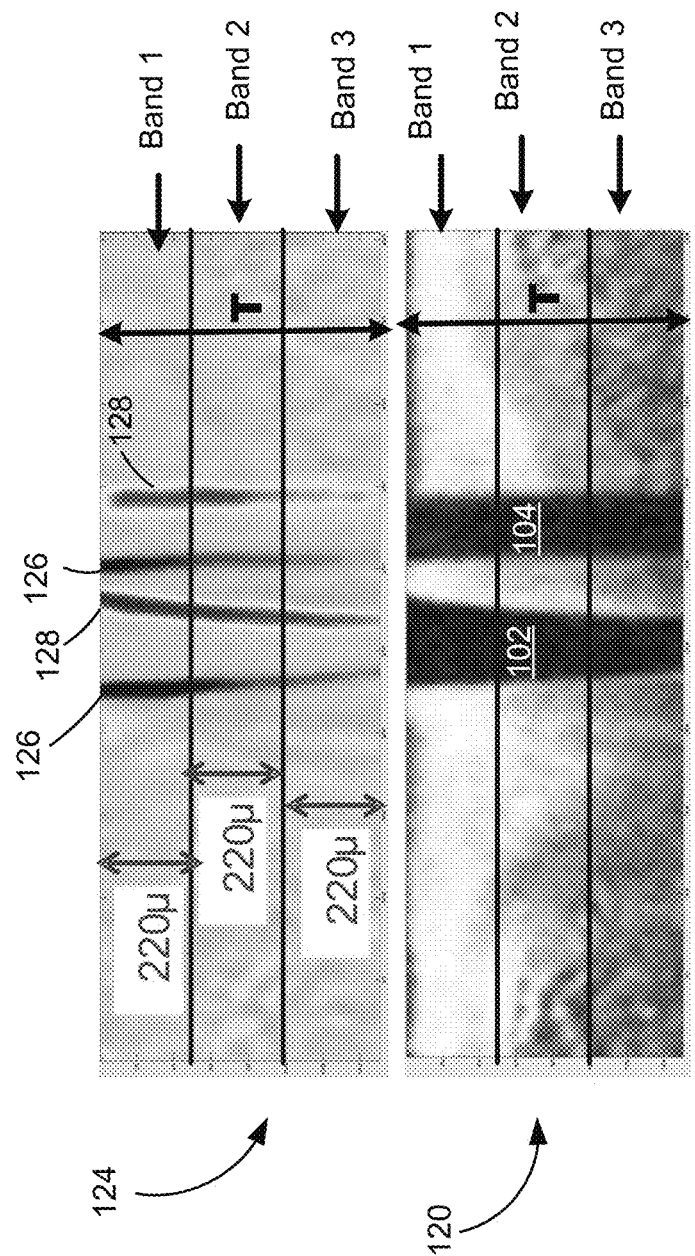
FIG. 6 is an image showing various bands or zones selected to search for side branches wherein the bands or zones are specified based on different depths from the lumen.

In one embodiment, the candidate regions are split into search bands or zones as shown in FIG. 6. In this way, the specification of the bands/zones to be searched facilitates determining candidate branching regions. In one embodiment, for each A-line it is divided into band 1, band 2, or band 3. The bands are a fraction of T in one embodiment. These bands identify which set of A-lines are potentially associated with a side branch. Each A-line is reviewed at three or more different depths with the depths shown as the divided bands of FIG. 6. Here there are three equal depths of 220 um, which correspond to ⅓ of T when T is 660 μm.

In one embodiment, as part of the selection/specification of regions to be searched, the region is split or subdivided into three bands (band 1, band 2, and band 3). In one embodiment, each band is processed separately. The bands can also be processed in parallel or differentially with features from one band being compared to features in one or more of the other bands. Although three bands are shown, one, two or more bands can be specified for candidate branch searching.

In one embodiment, for each specified search band the method accumulates marked pixels along each A-line. If a particular A-line has more than 10-35% pixels mark that A-line in that band as corresponding to branch. This approach implies at least 10-35% of the pixels in the search region were at or below the noise floor.

In one embodiment, the software modules are used to parse a branching matrix to isolate candidate branch regions that are most likely to be branches. This step is performed based on one or more rules for all three branching regions. The guidewire is removed in some embodiments.

In one embodiment, blood pooling and other sources of false branch positives is addressed. Thrombus, blood pooling and other artifacts represent major causes of false positives. The blood attenuates the signal, which can mimic the branching region. An intensity threshold that can identify the blood pooling pixels is calculated for each frame.

A blocking index is calculated based on the number of blood pooling pixels detected within the lumen for each detected branch. This index correlates to blood pooling and thrombus inside the lumen and provides a score for each detected branch. This index is high when there is a lot of signal attenuating blood or thrombus inside the lumen. Branches with a high Blocking Index are rejected as false positive. Those within an acceptable range are preserved as true positives. Branches with a mid-range blocking index can be flagged for further review.

Figure 7:
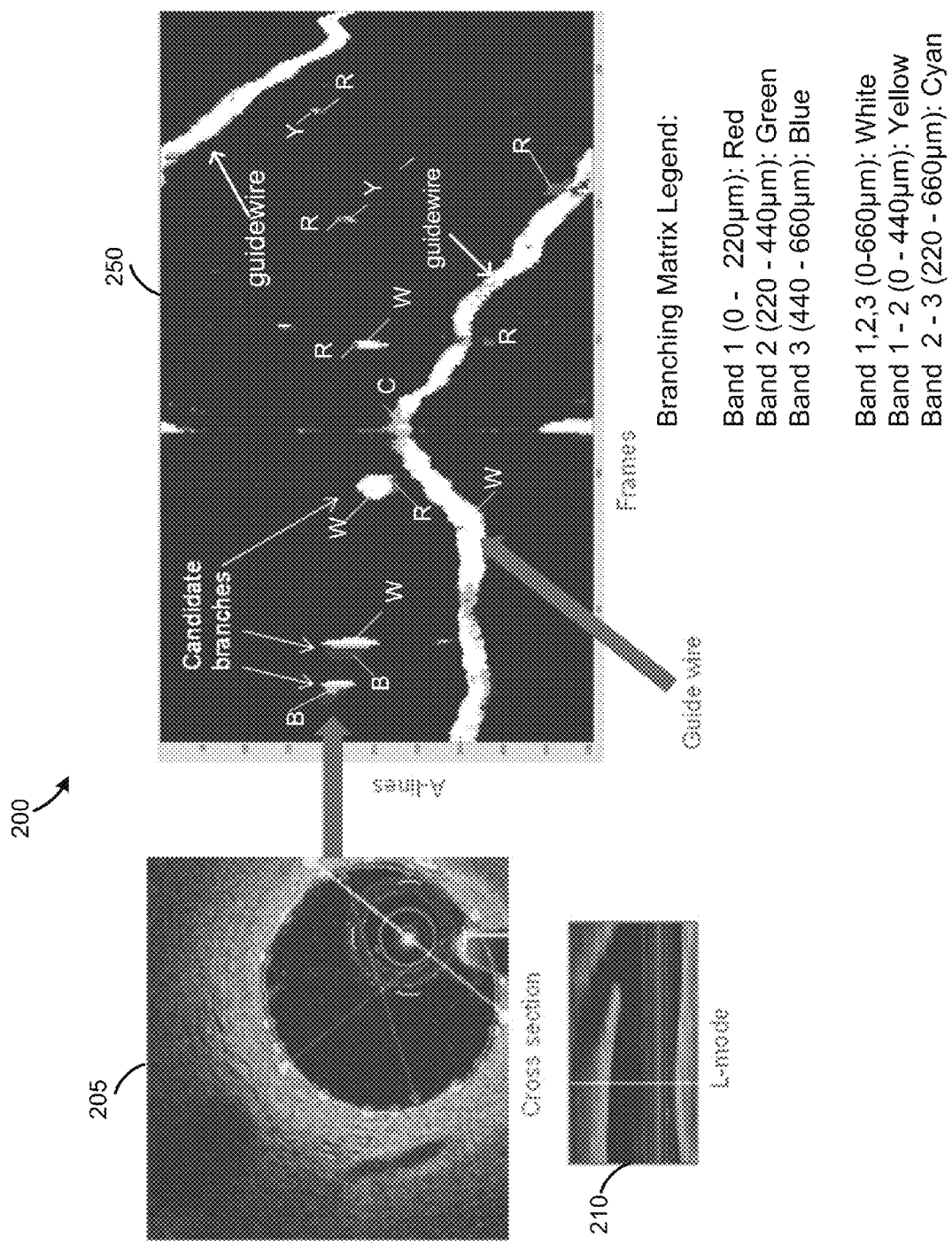
FIG. 7 is a cross-sectional OCT view, an L-mode or longitudinal OCT view, and a branching matrix with candidate branches and a guidewire.

FIG. 7 is a cross-sectional OCT view, a L-mode or longitudinal OCT view, and branching matrix with candidate branches and a guidewire. A color-coded legend of various detected depths is also shown. In general, the depth from the lumen is associated with a color and/or letter representative of the color for a range of depths. With regard to the parsed branching matrix of FIG. 7, the color red or R is for the range of from about 0 to about 220 µm. In turn, the color green or G is for the range of from about 220 µm to about 440 µm. The color blue or B is for the range of from about 440 µm to about 660 µm. The color yellow or Y is for the range of from about 0 to about 440 µm. Finally, the color cyan or C is for the range of from about 200 µm to about 600 µm. The color white or W corresponds to all three bands (bands 1, band 2 and band 3) and the overall distance T from the lumen such as for example 0-660 µm. These color coded indicia apply to FIGS. 7 and 8. Other indicia and symbols can be used to show the bands grouping other than color in various embodiments.

The branching matrix 250 and 300 (FIGS. 7 and 8, respectively) shows branch candidate information from all frames for all A-lines and for all 3 regions (bands 1, band 2 and band 3). With regard to the relationship of the different bands, the following legend of band groupings and colors applies to branching matrices 250, 300 of FIGS. 7 and 8. The colors are also identified by line connectors and the first letter of the color, but without an arrowhead to distinguish the use of letters A-E for showing candidate side branches.

Figure 8:
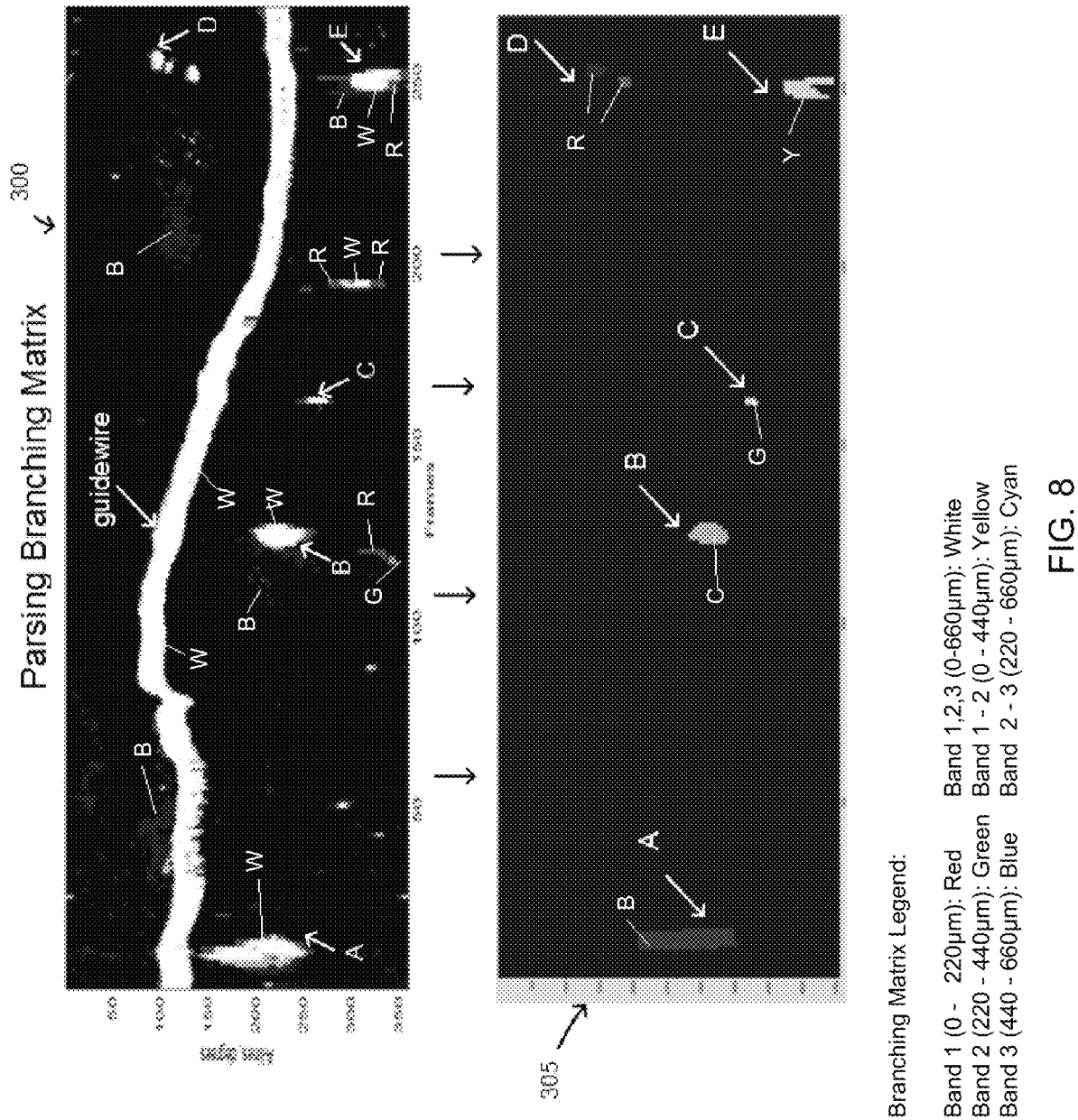
FIG. 8 is a branching matrix being parsed to identify various branch candidates in a processed or operated upon branching matrix according to an illustrative embodiment of the disclosure.

Branching Matrix Legend (distance from lumen/band groupings for example T=660 µm):

Band 1 (0-220 µm): Red (R)
Band 2 (220 µm-440 µm): Green (G)
Band 3 (440 µm-660 µm): Blue (B)
Bands 1, 2, 3 (0-660 µm): White (W)
Bands 1-2 (0-440 µm): Yellow
Bands 2-3 (µm 220-660 µm): Cyan FIG. 8 is a branching matrix 300 and the matrix after being operated upon 305. The matrix 300 is operated upon to remove guidewire data. After removal of guidewire data, matrix 305 shows candidate branches A, B, C, D, and E with the guidewire data removed. These branches are identified with arrows having arrow heads in images 300, 305. In one embodiment, one or more morphological operators are applied to further isolate and enhance matrix 305 such that branches are more clearly defined as shown in FIG. 305. The data from the branching matrix 300 can be compared with other cross-frame data to enhance detection accuracy. In one embodiment, a given branching matrix is assembled in a sequence on a per frame basis.

With respect to FIG. 8, the matrix 300 can be processed and operated to yield a processed or filtered matrix of branch candidates 305. These steps can include one or more the following processing or filtering steps. The method of detecting branches using a branching matrix can include generating a branching matrix. The method can include isolating pixels with white W (all 3 bands) and yellow Y (first two bands) pixels that neighbor white pixels. The method can include removing guide-wire regions.

The method may also include eliminating branches that appear only in 1 frame. In one embodiment, given that the angles span 360 degrees, depending on orientation and overlap of ends of matrix (it is based on a cylindrical arranged) sections of the matrix can be replicated to cover upper and lower horizontal axes of matrix. In one embodiment, the morphological operators can include the application of a 1D Image opening operation (7 pixels) along A-line dimension to eliminate a-lines with a negligible amount of data coverage. In addition, filters to emphasize connections can be applied to perform a connected component analysis to identify an individual component as a single branch. Cross frame data can also be used to connect blobs in the matrix that are part of one branch.

In part, the disclosure relates to an automated method of branch detection that includes the step of detecting branching characteristics within a region having a scan depth T. In one embodiment, T is a distance measured from the lumen and can be used to define a boundary offset by a distance T from the lumen boundary. In one embodiment, T ranges from about 400 µm to about 700 In one embodiment, T is about 660 In one embodiment, T is an approximation of a vessel wall thickness or a scan depth thickness selected to specify a search zone for finding side branches. In one embodiment, the branching characteristics include one or more of the following a noise floor or a signalless region between falling and rising gradients. The use of rising and falling segments relative to a noise floor as a detection signature advantageously improves detection accuracy with regard to large branches.

In one embodiment, the automated method of branch detection includes the step of combining candidate branching regions across all frames, substantially all frames or M frames, wherein M is 2 or more. In one embodiment, the automated method of branch detection includes the step of parsing the branching regions to identify candidate branches and estimating branch diameter of such candidate branches. In one embodiment, side branches having a diameter D greater than about 1 mm are tracked. In one embodiment, a large branch is a branch having a diameter D greater than or equal to about 1 mm.

Large branches make an increased contribution to flow and thus can significantly affect FFR, VFR, and other blood flow based measurements. As a result, once detected, branches having diameters of interest such as those greater than equal to about 1 mm, are tracked and evaluated to verify their characterization as a branch as opposed to a false detection such as a shadow. Other diameters of interest can include a branch diameter D that ranges from greater than about 0.4 mm to less than about 2 mm.

In one embodiment, the automated method of branch detection includes the step of generating a representative two-dimensional matrix of A-lines (also referred to as scan lines) versus frames to define a branching matrix. In one embodiment, the vertical axis is used to represent the A-lines with units of angles such as degrees ranging from 0 to 360 degrees and the horizontal axis has units corresponding to frame numbers. The angular range can be shown as greater than 360 degrees; however, the additional angle section of the matrix typically overlaps with earlier angular values in the matrix.

Accordingly, in one embodiment, the frame numbers can start at 0 or 1 and continue through J, wherein J is the number of frames in the pullback. The automated method of branch detection includes the step of parsing the branching matrix to isolate branch candidates. In one embodiment, guide wire detection and lumen detection are performed prior to performing branch detection. The guidewire visible in frames is removed in some embodiments.

A system of one or more computers can be configured to perform particular operations or actions by virtue of having software, firmware, hardware, or, a combination of them installed on the system that in operation causes or cause the system to perform the actions. One or more computer programs can be configured to perform particular operations or actions by virtue of including instructions that, when executed by data processing apparatus, cause the apparatus, computing device, to perform the actions.

One general aspect includes a method of automatically detecting one or more side branches that includes generating a branching matrix comprising scan line data and frame designators. The method also includes storing, using an intravascular imaging system, one or more intravascular image datasets of the blood vessel; each intravascular dataset including a plurality of A-lines. The method also includes generating an A-line image with a detected lumen boundary of the blood vessel. An offset T can also be used to shift a representation of a detected lumen in a direction away from the imaging probe into a tissue or branch region.

In one embodiment, the method also includes increasing intensity of edges in A-line image. The method also includes suppressing smooth regions in A-line image. The method also includes specifying a search distance T offset relative to the lumen. The offset T can define a region or band to search for candidate side branch regions. The method also includes identifying local min-max pairs in a filtered image. In one embodiment, the method also includes searching the radial dimension r in the corresponding pre-processed input image.

In one embodiment, the method also includes marking pixels below noise floor threshold in the pre-processed input image as candidate branching regions. Other embodiments of this aspect include corresponding computer systems, apparatus, and computer programs recorded on one or more computer storage devices, each configured to perform the actions of the methods.

Implementations may include one or more of the following features. The method further including: flattening the A-line image using a first image processing operator. The method may also include applying median smoothing to A-line image using a second image-processing operator. The method may also include applying Gaussian smoothing to A-line image using a third image-processing operator.

In one embodiment, the method further includes dividing the candidate branching regions into N bands, such as 1, 2, 3 or more bands and processing each band separately. In one embodiment, the bands have the same thickness. In one embodiment, the thickness or width of a band is T/N for N bands. The method further includes accumulating marked pixels along each A-line. The pixels can be marked or otherwise tracked using software to identify a given pixel as corresponding to a shadow, a guidewire pixel, a branch pixel such as a side branch pixel, a lumen pixel, a blood pixel and other pixels corresponding to imaged intravascular objects or shadows or reflections thereof.

In one embodiment, if a particular A-line has more than between about 10% and about 30% pixels marked as a branch, the method marks the A-line in that band as a branch or an A-line containing branch. The method further includes generating a branching matrix during frame by frame processing. The method further includes isolating pixels with white (all 3 bands) and yellow (first two bands) pixels that neighbor white pixels. The method further includes removing guidewire region. The method further includes eliminating branches that appear only in one frame. Thus, failure of a branch to appear in multiple frames can be used to exclude candidate branches. The method further includes replicating branching matrix to account for overlap across zero. Implementations of the described techniques may include hardware, a method or process, or computer software on a computer-accessible medium.

Although the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation and steps from various methods can be combined without limitation. Notwithstanding the foregoing and the other disclosure herein, embodiments disclosed herein may also be applied in the context of bi-polar based systems and methods as applicable.

Non-Limiting Software Features and Embodiments for Implementing Branch Detection The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "angling" or "selecting" or "toggling" or "calculating" or "comparing" or "arc length measuring" or "detecting" or "tracing" or "masking" or "sampling" or "operating" or "generating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure, in some embodiments, also relates to the apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present disclosure, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, FFR data, IVUS data, co-registration data, pixels, branching matrixes, and orientation and coordinates, user interface signals, and various graphical display elements and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

It should be appreciated that various aspects of the claimed disclosure are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the disclosure claimed. Accordingly, what is desired to be secured by Letters Patent is the disclosure as defined and differentiated in the following claims, including all equivalents.

The term "machine-readable medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

It can be appreciated that, in certain aspects of the disclosure, a single component may be replaced by multiple components, and multiple components may be replaced by a single component to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

What is claimed is:

1. A method of detecting one or more branches of a blood vessel comprising storing one or more intravascular image datasets of the blood vessel, each intravascular dataset comprising a plurality of A-lines;
   detecting a lumen boundary in a first A-line image generated from a set of A-lines from the plurality of A-lines, wherein the first A-line image has an r dimension and an A-line dimension;
   specifying a search distance T;
   defining a search region, the search region bounded by the detected lumen boundary and a boundary offset therefrom by distance T;
   detecting edges in the search region; and
   identifying candidate branching region in response to the detected edges.

2. The method of claim 1 further comprising:
   flattening the A-line image using a first image processing operator;
   applying median smoothing to A-line image using a second image processing operator; and
   applying smoothing to A-line image using a third image processing operator to generate a filtered image.

3. The method of claim 2 further comprising:
   identifying a first minimum-maximum pair in the filtered image, wherein one or more distances between the first minimum-maximum pair defines a first search window.

4. The method of claim 3 further comprising:
identifying a second minimum-maximum pair in the filtered image, wherein one or more distances between the second minimum-maximum pair defines a second search window.

5. The method of claim 3 further comprising:
searching along r dimension in corresponding pre-processed input image within first search window.

6. The method of claim 5 further comprising: designating pixels below noise floor threshold located in the first search window as corresponding to the candidate branching region.

7. The method of claim 5 wherein the noise floor threshold is less than about 2 mm.

8. The method of claim 6 further comprising: splitting the candidate branch region into three bands, wherein sum of widths of three bands is equal to T.

9. The method of claim 8 further comprising: for each band, accumulating pixels along each A-line that correspond to the candidate branching region.

10. The method of claim 9, wherein if a particular A-line has more than between about 10% and about 30% pixels marked as a candidate branch, mark that A-line in that band as corresponding to a branch.

11. The method of claim 10, further comprising outputting set of A-lines for each band that correspond to a candidate branch.

12. The method of claim 3 further comprising generating a branching matrix using frames of a pullback, the frames comprising A-lines and angular data.

13. The method of claim 12 further comprising isolating pixels corresponding to a grouping of all three bands and a grouping of first two bands to select pixels corresponding to a side branch.

14. The method of claim 12 further comprising removing a guidewire region from the branching matrix.

15. The method of claim 14 further comprising eliminating branches that appears only in one frame.

16. The method of claim 12 further comprising replicating branching matrix to account for overlap across zero.

17. The method of claim 13 wherein the first band ranges from 0 to T/3, and wherein second band ranges from T/3 to ⅔T, and wherein third band ranges from ⅔T to T.

18. The method of claim 8 wherein the first band ranges from 0 to T/3, and wherein second band ranges from T/3 to ⅔T, and wherein third band ranges from ⅔T to T.

19. The method of claim 8 further comprising displaying one or more detected side branches in a user interface.

20. The method of claim 1 further comprising validating one or more candidate side branches using a branching matrix, the branch matrix generated using pixel selected from two or more bands, wherein the sum of the bands is T.

* * * * *